United States Patent [19]

Geluk et al.

[11] Patent Number: 5,350,871

[45] Date of Patent: Sep. 27, 1994

[54] METHOD OF PREPARING OPTICALLY ACTIVE CYANOHYDRINS

[75] Inventors: Hendrik W. Geluk; Wybrand T. Loos, both of Weesp, Netherlands

[73] Assignee: Duphar International Research B.V., Weesp, Netherlands

[21] Appl. No.: 986,784

[22] Filed: Dec. 8, 1992

[30] Foreign Application Priority Data

Dec. 11, 1991 [EP]  European Pat. Off. ........ 91203241.4

[51] Int. Cl.$^5$ .................. C07C 253/00; C07C 253/30
[52] U.S. Cl. .................................. 558/351; 435/128; 546/176; 546/330; 548/561; 549/75; 549/491
[58] Field of Search ...................... 558/351; 435/128; 546/176, 330; 548/561; 549/75, 491

[56] References Cited

U.S. PATENT DOCUMENTS 4,859,784  8/1989  Effenberger et al. ............... 549/491
5,122,462  6/1992  Miethe et al. ....................... 435/128

FOREIGN PATENT DOCUMENTS 0322973  7/1989  European Pat. Off. .
1300111  7/1969  Fed. Rep. of Germany .
1593260  9/1969  Fed. Rep. of Germany .

OTHER PUBLICATIONS

Ognyanov et al, Journal of the American Chemical Society, vol. 113 (1991) pp. 6992–6996.
J. Am. Chem. Soc., (1966), 88, pp. 4299–4300, W. Becker et al., "Continuous Synthesis of Optically Active α-Hydroxynitriles".
Angew. Chem., (1965), 77, p. 1139, Becker et al., "Stereospezifische Synthese von D–Hydroxynitrilen und optisch aktiven Äthanolaminen".
Tetr. Lett., (1988), 29, pp. 4485–4488; J. Brussee et al., "Bio–Organic Synthesis of Optically Active Cyanohydrins and Acyloins".
Tetrahedron (1990), 46, pp. 979–986, J. Brussee et al., "Synthesis of Optically Active Silyl Protected Cyanohydrins".
Angew. Chemie (1987), 99, pp. 491–492, Franz Effenberger et al., "Enzymkatalysierte Cyanohydrin–Synthese in organischen Lösungsmitteln".
Chem Tech. (1986), 16, pp. 354–359, Alexander M. Klibanov, "Enzymes that work in organic solvents".
Acc. Chem. Res., (1990), 23, pp. 114–120, Alexander M. Klibanov, "Asymmetric Transormations Catalyzed by Enzymes in Organic Solvents".
Chemical Abstracts, vol. 87 (1977), p. 278, abstract No. 87:129560h, Klibanov, A. M., "A new approach to preparative enzymic synthesis".
Synthetic Communications, 21 (12 & 13), pp. 1387–1391 (1991), Zandbergen et al., "Synthesis of Optically Active Cyanohydrins Using Almond Meal".
Tetrahedron Letters, vol. 31, No. 9, pp. 1249–1252, (1990), Effenberger, et al, "Enzyme-Catalyzed Synthesis of (S)–Cyanohydrins and Subsequent Hydrolysis to (S)–α–Hydroxy–Carboxylic Acids".

Primary Examiner—Joseph Paul Brust
Attorney, Agent, or Firm—Stevens, Davis, Miller & Mosher

[57] ABSTRACT

The invention relates to a method of preparing an optically active cyanohydrin by addition of hydrogen cyanide to a carbonyl compound, selected from aldehydes and ketones, in the presence of hydroxynitrile lyase, in a biphasic solvent system, comprising a homogeneous aqueous solution of said enzyme, and a suitable organic solvent which is at least substantially immiscible with water. Said method is performed in that said homogeneous aqueous solution is buffered with an acetate buffer having a buffer concentration of between 0.005 and 0.1 mole per liter or with a non-acetate buffer, that the volume ratio organic phase:aqueous phase is between approx. 5:1 and approx. 1:5, and that a solution of hydrogen cyanide and said carbonyl compound in said organic solvent is properly mixed during the reaction period with said homogeneous aqueous solution of hydroxynitrile lyase.

12 Claims, No Drawings

METHOD OF PREPARING OPTICALLY ACTIVE CYANOHYDRINS

The invention relates to a method of preparing optically active cyanohydrins by the addition of hydrogen cyanide to aldehydes or ketones in the presence of hydroxynitrile lyase.

Cyanohydrins are versatile starting compounds or intermediates for the production of biologically active substances, which may be used e.g. in pharmaceutical compositions, for human or veterinary application, or in crop protection agents. Various of such active substances contain one or more chiral centers in their molecular structure, and therefore give rise to optical isomerism. It is generally known in the art, that often only one of the enantiomers presents the desired biological activity. The presence of the other optical antipode in a composition or agent may cause or invigorate certain side effects and burden the recipient, viz. the human or animal body, or the environment, respectively. It is generally deemed more and more desirable to administer the biologically active substance in the form of a substantially single optical isomer, which specifically exhibits the desired biological activity, the so-called eutomer, and not in the form of a mixture of optical isomers, containing also the other, differently behaving antipods, the so-called distomer, in a substanitial amount. Cyanohydrins may also be used for the production of other technically important materials for which high enantiomeric purities are required, such as liquid crystals.

In connection with the above there is an increasing number of publications in the field of producing optically active cyanohydrins reflecting the growing demand for these compounds as starting compounds or synthetic building blocks for the production of biologically active substances. For decades it is already known that the class of hydroxynitrile lyases catalyses the formation of specific optically active cyanohydrins by the addition of hydrogen cyanide to the corresponding carbonyl compounds.

Because the enzyme hydroxynitrile lyase is a water soluble protein, whereas the organic substrates, viz. the starting carbonyl compounds, are generally only poorly water-soluble, it is obvious to investigate the applicability of organic solvents for the enzymatic synthesis of cyanohydrins.

The use of water-miscible organic solvents to improve the solubility of the substrate and of the product has been reported in the literature, viz. by Becker et al (DE-A-1,300,111; DE-A-1,593,260; J.Am.Chem.Soc., 1966, 88, 4299; Angew. Chem., 1965, 77, 1139) and by Brussee et al (EP-A-322973; Tetr. Lett., 1988, 29, 4485; Tetrahedron 1990, 46, 979). Especially the use of methanol or ethanol as a co-solvent with water is frequently mentioned. Effenberger et al (Angew. Chemie 1987, 99, 491–492) have demonstrated that, dependent on the starting aldehyde, the stereochemical purity of the desired cyanohydrin is often unsatisfactory in case the enzyme-catalyzed conversion is carried out in a water-/ethanol mixture. As will become apparent from the examples hereinafter, substitution of other water-miscible organic solvents such as dimethylformamide for the above alcohols in this solvent mixture does not substantially improve the selectivity or efficiency of said conversion.

In reviews by Klibanov (ChemTech., 1986, 16, 354–359; Acc. Chem. Res., 1990, 23, 114; Biotechnology and Bioengeneering, 1977, 19, 1351) lipophylic solvents, e.g. hydrocarbons, are recommended as organic solvents for many enzymatic conversions. It has been found, however, that the use of non-polar water-immiscible organic solvents, such as hexane, toluene or chlorinated hydrocarbons, adversely affects the stability and/or activity of hydroxynitrile lyase. As a result, the enzyme is significantly less productive in such systems, which handicaps a commercially acceptable application of such systems for the production of optically active cyanohydrins.

From EP-A-276375 it is known, that the conversion of certain aldehydes with hydrogen cyanide can be carried out in the presence of immobilized hydroxynitrile lyase in a reaction mixture consisting of a water-immiscible organic solvent, saturated with an aqueous buffer solution. It is mentioned, that suitable organic solvents for the described conversion are aliphatic hydrocarbons such as petroleum ether, aromatic hydrocarbons such as benzene or toluene, chlorinated aliphatic hydrocarbons such as methylene chloride, ethers such as diethyl ether, carboxylic alkyl esters such as acetic acid esters, and aliphatic water-immiscible alcohols such as n-butanol. The enzyme is immobilized on cellulose or chemically modified cellulose or on another carrier material by precipitation or adsorption. In the examples of the last-mentioned patent application, ethyl acetate is mainly used as the organic solvent. This is also the solvent of choice in the publication of Effenberger et al., mentioned hereinbefore. In a recent publication by the same authors (Tetr. Lett., 1990, 31, 1249–1252), both diisopropyl ether and ethyl acetate are considered to be suitable organic solvents for the above conversion, wherein, as mentioned above, the enzyme has been adsorbed or precipated on cellulose, viz. Avicel-cellulose ®.

It has been observed, however, that following the procedure for immobilizing the enzyme, viz. the hydroxynitrile lyase, as required for the above-mentioned method of cyanohydrin synthesis, a considerable amount of enzyme activity is lost. This results in a dramatic reduction of the operational effectiveness of the enzyme, as will be apparent from the Examples. Another phenomenon, which has been observed in using immobilized hydroxynitrile lyase as used by Effenberger et al. (vide supra), is the pronounced sensitivity of the enzyme activity to the moisture content. The criticallity of the moisture content of the immobilized enzyme requires an accurate control of the reaction system. Further, the use of neat HCN, a notorious toxic substance, in considerable quantities, necessitates specific production facilities and special safety requirements, which make the process more expensive.

In a corresponding manner the enzymatic conversion of oxo compounds with prussic acid in the presence of oxynitrilase is disclosed in EP-A-446826. The enzyme used is solubilized in a iyotropic liquid crystal, using certain tensides for the liquid crystal formation. organic solvent, aqueous buffer and tenside form a ternary system. As will be apparent from the Examples, the effectiveness of this enzymatic system is insufficient for a technically attractive realization of the enzymatic conversion.

In a recent publication by Zandbergen et al. (Synth. Commun. 1991, 21, 1387–1391), the preparation of optically active cyanohydrins under the influence of crude almond meal instead of isolated enzyme is described. The reactions described were carried out in an organic solvent, viz. ethyl acetate, wherein the almond meal, swollen with a little citrate buffer, was suspended. The reaction times were extremely long, viz. varying between 16 and 89 hours, yielding products with unspecified cyanohydrin purities. The use of an undefined starting material, viz. almond meal, in such large quantities, viz. 150 wt. % on substrate, has distinct disadvantages: (i) the quality and consequently the enzyme content, as well as the amount and character of the contaminants (non-enzymatic material and other enzymes) may vary widely; (ii) organic material may seriously contaminate the final product; (iii) the work-up procedure will be seriously complicated by the presence of said contaminants; and (iv) said contaminants should be disposed of, and therefore form an environmental burden.

In view of the above drawbacks it might be advantageous to carry out the cyanohydrin synthesis in the presence of a solubilized enzyme in a biphasic solvent system consisting of a water-immiscible organic solvent and a homogeneous aqueous phase. However, according to Effenberger et al. (vide supra), the competing non-enzymatic reaction producing racemic cyanhydrins by addition of hydrogen cyanide to the starting carbonyl compounds in the aqueous phase may cause an undesired decrease of the enantiomeric purity of the product.

The results as recently presented by Ognyanov et al. (J.Amer.Chem.Soc. 1991, 113, 6992–6996) reveal the disadvantage of the use of free hydrogen cyanide in a biphasic system for the preparation of enantiomerically pure cyanohydrins. The problem related to the use of free hydrogen cyanide as recognized by Ognyanov et al. was circumvented by a hydroxynitrile lyase mediated transcyanation, using acetone cyanohydrin in a biphasic reaction mixture, consisting of an aqueous buffer solution and a water-immiscible organic solvent, viz. diethylether. After a reaction time of several hours, products could be obtained in yields of up to approx. 70% and generally showing enantiomeric purities of at least 90%. In a typical example, benzaldehyde was converted after a reaction time of 10 hours to R-mandelonitrile in a yield of 72% and an enantiomeric excess (ee) of 92%. These results were obtained by adding the hydroxynitrile lyase in an acetate buffer solution to a mixture of the starting aldehyde and acetone cyanohydrin dissolved in diethylether, followed by stirring at ambient temperature.

The above-described process, however, displays the following disadvantages for a technical and commercial realization of the process. The volume of the organic solvent and consequently of the total reaction mixture is large with respect to the quantity of the aldehyde to be converted. Furthermore the reaction times are extremely long, which also limits the yield of production. The quantity of the enzyme needed for the enantiospecific conversion is high. This means that a large amount of expensive enzyme is required for the conversion, which may be lost in the work-up procedure. Last but not least, the optical purity of the cyanohydrin obtained is generally unsatisfactory for use in the enantiospecific synthesis of target molecules. For most applications an enantiomeric excess (ee) of at least 95% is desired or even required.

It is the object of the present invention to provide a method of preparing optically active cyanohydrins as defined above, wherein the conversion is carried out in a smaller solvent volume, in a shorter reaction time, with a smaller amount of enzyme, with sufficient enzyme recycling possibilities and consequently a smaller enzyme consumption, and, last but not least, with a higher optical purity and yield, and with an easy work-up.

This object can be achieved by a method of preparing an optically active cyanohydrin as defined above, namely by the addition of hydrogen cyanide to a carbonyl compound, selected from aldehydes and ketones, in a biphasic solvent system, comprising a homogeneous aqueous solution of hydroxynitrile lyase, and a suitable organic solvent which is at least substantially immiscible with water, which method is characterized according to the present invention, in that said homogeneous aqueous solution is buffered with an acetate buffer having a buffer concentration of between 0.005 and 0.1 mole per liter or with a non-acetate buffer, that the volume ratio organic phase:aqueous phase is between approx. 5:1 and approx. 1:5, and that a solution of hydrogen cyanide and said carbonyl compound in said organic solvent is properly mixed during the reaction period with said homogeneous aqueous solution of hydroxynitrile lyase.

The method of the invention, using a biphasic solvent system, works suprisingly well when hydrogen cyanide is used for the cyanohydrin synthesis under the above-defined conditions. This is contrary to expectation in view of what is reported by Ognyanov et al., viz. on page 6993 of J. Amer. Chem. Soc. 1991, 113. Hydrogen cyanide, dissolved in an organic solvent, is easily available for the desired reaction by an extraction procedure using an alkali cyanide as the cyanide source. In this manner a solution of HCN in an organic solvent can easily be prepared in situ, so that the handling of neat HCN can be avoided. As opposed to HCN-releasing agents such as acetone cyanohydrin, hydrogen cyanide should be considered as the most convenient reagent from an economical point of view. Furthermore it can easily be removed, recycled or decomposed.

As will become apparent from the appendant Examples, the process of the invention can be performed in approximately ten percent of the solvent volume indicated by Ognyanov et al. (vide supra) and commonly well within one hour of reaction time, and by using only approximately ten percent of the enzyme quantity as reported by Ognyanov et al. Proper mixing is required to ensure sufficient interfacial area between the phases; this can be effected by mechanical stirring. When the cyanohydrin synthesis is carried out under the conditions of the present invention, the enzyme presents a high activity, resulting in a high conversion and a selectivity of more than 95% of the desired cyanohydrin enantiomer. Moreover, high concentrations of starting carbonyl compound in the organic solvent can be used without adversely influencing the yield or optical purity.

Optimum results are obtained by performing the conversion of the present invention in a biphasic solvent system, wherein the volume ratio organic phase:aqueous phase varies between approx. 3:1 and approx. 1:3.

As mentioned above, in case an acetate buffer is used, this buffer should have a concentration of 0.1 mole per liter at most to achieve satisfactory results. It is of advantage, however, to use a nonacetate buffer, preferably in a concentration of between 0.005 and 0.5 mole per liter. The best results are obtained at a buffer concentration of between 0.01 and 0.2 mole per liter. The nonacetate buffer is preferably selected in such a manner, that the pH of the buffer solution is between 3 and 6, preferably between approx. 4 and approx. 5.5. Suitable non-acetate buffers to be used in the method of the invention are citrate, succinate, glutamate and phthalate buffers. The reaction temperature may vary, dependent on the substrate and the other reaction conditions used; generally a reaction temperature between approx. 0° C. and approx. 30° C. is suitable for the desired conversion.

In a pre-eminently convenient embodiment, the process of the invention is performed in such a manner, that to a solution of hydrogen cyanide in the organic solvent, obtained by extraction of an aqueous alkali metal cyanide solution with the organic solvent, are successively added the homogeneous buffer solution of hydroxynitrile lyase and the carbonyl compound, after which the biphasic reaction system thus obtained is properly mixed, e.g. by stirring, during the reaction period. It will be evident from the Examples, that this simple and fast "one-pot" reaction yields the desired optically active cyanohydrin in a high enantiomeric purity. Therefore, this preferred process lends itself admirably to a technically and commercially attractive realization.

Dependent on the material from which the enzyme hydroxynitrile lyase is isolated, different enzymes can be obtained to be used for the above cyanohydrin synthesis, viz. R- and S-hydroxynitrile lyase (E.C.4.1.2.10 and E.C-4.1.2.11). These enzymes differ significantly in substrate specificity and biocatalytic activity. Dependent on the substrate, i.e. the starting carbonyl compound, and the desired cyanohydrin enantiomer, the most suitable hydroxynitrile lyase can be selected. The required enzyme quantity will depend on the substrate used. Usually optimum results can even be obtained when hydroxynitrile lyase is used in a quantity of 1.5 mg per mmol of substrate at most.

The choice of the organic solvent for the above defined reaction according to the present invention is crucial for high yields and high enantiomeric purities of the products. Therefore the organic solvent used in the biphasic solvent system of the present invention is preferably selected from the group consisting of di($C_1$-$C_6$)alkyl ethers, ($C_1$-$C_5$)carboxylic ($C_1$-$C_5$)alkyl esters, di($C_1$-$C_5$)alkyl ketones, ($C_4$-$C_8$)aliphatic alcohols, and mixtures of these solvents with each other or with apolar diluents. Suitable examples of such water-immiscible solvents are: diethyl ether, di-n-propyl ether, di-isopropyl ether, di-n-butyl ether, di-isobutyl ether, methyl-t-butyl ether, ethyl acetate, n-propyl acetate, isopropyl acetate, isomeric butyl acetates, isomeric amyl acetates, methylethylketone, diethylketone, and methylisobutylketone. Most preferred are: n-propyl acetate, isopropyl acetate, n-butyl acetate, isobutyl acetate, sec.butyl acetate and amyl acetate.

Suitable examples of apolar diluents are aromatic hydrocarbons, aliphatic hydrocarbons and chlorinated aromatic or aliphatic hydrocarbons, such as toluene, xylene, hexane, cyclohexane, trichloroethene or chlorobenzene.

For a technical realization of the process of the present invention it is desirable to avoid the use of large amounts of organic solvents. Therefore the concentration of the starting carbonyl compound in the organic solvent, as defined above, is preferably more than 5% wt./vol.

Furthermore it has been found, that the enzyme containing aqueous phase can be recycled surprisingly simply, so that a cascade or continuous process for producing optically active cyanohydrins is within the scope of the present invention. This recycling, as illustrated in the Examples, offers the possibility to reuse the aqueous phase after the reaction is complete once or repeatedly. For this purpose, after the reaction period the aqueous phase can be separated from the organic phase and be reused as such, viz. by properly mixing said aqueous phase with a fresh solution of hydrogen cyanide and said carbonyl compound in the organic solvent during another reaction period.

A variety of carbonyl compounds can be used as substrates for the addition reaction of the invention, for example optionally substituted (hetero)aromatic aldehydes such as benzaldehyde, fluorobenzaldehyde, hydroxybenzaldehyde, phenoxybenzaldehyde, methoxybenzaldehyde, furfural, methylfurfural, nicotinaldehyde and piperonal, saturated or unsaturated aliphatic aldehydes such as crotonaldehyde, methylthiopropionaldehyde, pivaldehyde, ($C_1$-$C_6$)alkoxy-acetaldehyde and isomeric butyraldehydes, and optionally substituted aralkyl aldehydes such as (subst.) phenylacetaldehyde and phenoxyacetaldehyde. Suitable substituents for the above carbonyl compounds are ($C_1$-$C_4$)alkyl, hydroxy, ($C_1$-$C_4$)alkoxy, phenoxy, halogen and hydroxy($C_1$-$C_4$)alkyl.

Equally suitable as substrates for the desired reaction are the compounds described in EP-A-322973 and having the general formula

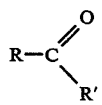

wherein: R is a monocyclic or bicyclic aryl or heteroaryl group substituted with one or more substituents, selected from hydroxy, ($C_1$-$C_5$)alkoxy, phenoxy, ($C_1$-$C_5$)alkylcarbonyloxy, amino, ($C_1$-$C_5$)alkylamino, di($C_1$-$C_5$alkylamino, ($C_1$-$C_5$)alkylsulphonyl, ($C_1$-$C_5$)alkylcarbonyl, halo, cyano, ($C_1$-$C_5$)alkyl, ($C_3$-$C_6$)cycloalkyl and ($C_3$-$C_2$)alkylenedioxy or wherein R is a saturated or unsaturated straight or branched alkyl group having 1-30 C-atoms which may be substituted with halogen, ($C_1$-$C_5$)alkoxy, ($C_1$-$C_5$)alkylthio, phenyl or phenoxy optionally substituted with one or more of the above-defined substituents; and wherein R' is a hydrogen atom or a ($C_1$-$C_4$)alkyl group.

Monocyclic or bicyclic (hetero)aryl encompasses phenyl, naphthyl, furyl, pyridyl, quinolyl, thienyl, pyrrolyl, and the phenylene-annelated derivatives of the last-mentioned heteroaromates.

The most useful parameter to the practical usefulness of an enzyme in a certain enzymatic conversion is the operational effectiveness factor $\eta_0$. See in this connection e.g. the Handbook of Enzyme Biotechnology, 2nd. ed., ed. A. Wiseman, 1986, pp.93-94. The effectiveness factor clearly indicates the effectiveness of an enzyme under the reaction conditions applied, in comparison with conditions that are considered as ideal for the enzyme. Therefore the operational effectiveness factor is excellently suitable to compare the useful application, in particular on an industrial scale, of relatively expensive biocatalysts, such as the above enzyme hydroxynitrile lyase, under various conditions.

In the specific examples below the effectiveness factor $\eta_0(50)$ is used, i.e. the operational effectiveness determined at 50% conversion. This effectiveness factor is defined by $$\eta_0(50) = \overline{V}(50)/V_{max}$$

wherein V(50) is the activity measured at 50% conversion of the substrate to the product under the reaction conditions. $V_{max}$ is a known parameter and denotes the maximum initial activity on an ideal substrate under optimum conditions. The $V_{max}$ value for almond hydroxy-nitrile lyase is 1360 addition units (add.units) per mg enzyme, based on a maximum "turnover number" for mandelonitrile formation of 102000 (min$^{-1}$) and a molecular weight of 75000 (A. Schuman Jorns, Biochim Biophys. Acta, 1980, 613, 203–209):

$$V_{max} = 102000/75 = 1360 \text{ add. units}$$

The parameter "addition unit" (add. unit) is defined as follows: 1 add. unit is the amount of enzyme which converts 1 μmol of carbonyl compound (in the presence of HCN) into the corresponding cyanohydrin per minute under standardized conditions.

So in the experiment described by Ognyanov et al. (see above), $\eta_0(50)$ can be calculated as follows: 5 mg of the enzyme preparation used (Sigma MO646®) contains 2 mg almond hydroxynitrile lyase. It is optimistically presumed that 50% conversion (500 mol) is reached after 10% of the total reaction time, i.e. after 1 hour.

$$\overline{V}(50) = 500/(60 \times 2) = 4.17^*$$
$$\eta_0(50) = 4.17/1360 = 0.003$$

*In the Examples the parameter $\overline{V}(50)$ is denoted in the following units: moles substrate per minute per mg enzyme.

In addition to the conversion of the substrate, the enantiomeric purity (ee) of the cyanohydrin obtained and the enzymatic conversion ($\eta_0$), an additional parameter is important for a technically and commercially attractive realization of the process of the invention, viz. the production capacity. The production capacity can be expressed conveniently in moles of converted substrate per liter of reactor feed per hour, the so-called "throughput". As will be clear from the Examples, by using the method of the invention a throughput of at least approximately 1 (in mol.l$^{-1}$.h$^{-1}$), even nearly approximately 10, can be realized, which is clearly considerably higher than the throughput calculated for any of the known processes. The throughput in the process described by Ognyanov et al. (see above) is 0.01.

The invention will now be described in greater detail with reference to the following specific Examples.

EXAMPLE I

Benzaldehyde in a quantity of 3.18 g (30 mmol) and 2.43 g HCN (90 mmol) are dissolved in 25 ml of methyl tert.-butyl ether (MTBE). To this solution are successively added 24.5 ml 10 mM aqueous citrate buffer solution (pH 5.0) and 0.5 ml of enzyme solution comprising 7.2 mg pure R-hydroxynitrile lyase. So the enzyme concentration (in mg enzyme/mmol aldehyde) is 0.24 mg/mmol. Stirring for 20 minutes at room temperature with a convenient mechanical stirrer. Then the two liquid phases are separated, the aqueous layer is extracted with 25 ml MTBE and the combined organic phases are worked up in a conventional manner, yielding the desired cyanohydrin in a yield of 98% based on starting aldehyde. The enantiomeric excess ("ee") is determined by HPLC and amounts to 96%; 50% conversion is reached after 2.6 minutes. V(50) is determined from the above results:

$$\overline{V}(50) = 15.10^3/(2.6 \times 7.2) = 801 \text{ (μmol substr. min}^1. \text{ mg enzyme}^1)$$

$$\eta_0(50) = 801/1360 = 0.59$$

The throughput is 1.8 (mol.l$^{-1}$.h$^{-1}$).

EXAMPLE II

In a corresponding experiment as described in Example I, a solution of 3.37 g benzaldehyde (31.8 mmol) in 10 ml MTBE and 2.43 g HCN (90 mmol) are made up with MTBE to a volume of 25 ml. To this solution are successively added 25 ml 0.1M citrate buffer (pH 5.5) and 750 l enzyme solution, containing 10.8 mg pure R-hydroxynitrile lyase. So the enzyme concentration is 0.34 mg enzyme per mmol aldehyde. Stirring during 20 minutes and working up as described above yields 83% of the desired cyanohydrin; 96% ee; 50% conversion after 1.5 min.

$$\overline{V}(50) = 15900/(1.5 \times 10.8) = 981$$

$$\eta_0(50) = 981/1360 = 0.72$$

Throughput: 1.9.

In a corresponding manner as described in Example I, but under varying reaction conditions (temp. T, pH, enzyme concentration—in mg/mmol substrate), cyanohydrin enantiomers are prepared from the following substrates. Yields of product and purities, as well as the relevant reaction conditions, are given in Table A below.

TABLE A

| substrate | reaction conditions | | | R-cyanohydrin | |
|---|---|---|---|---|---|
| | T(°C.) | pH | enzyme conc. | yield (%) | ee (%) |
| 4-fluorobenzaldehyde | 10 | 5.5 | 0.50 | 97 | 99 |
| 4-methoxybenzaldehyde | 20 | 5.0 | 0.29 | 88 | 94 |
| piperonal | 20 | 5.0 | 0.41 | 91 | 98 |
| 5-methylfurfural | 20 | 4.5 | 0.34 | 86 | 99 |
| crotonaldehyde | 20 | 4.5 | 0.67 | 97 | 97 |
| n-butyraldehyde | 20 | 4.5 | 0.37 | 99 | 98 |
| i-butyraldehyde | 10 | 4.5 | 1.50 | 99 | 93 |
| phenylpropionaldehyde | 10 | 4.5 | 1.50 | 98 | ca.90 |

Example III

To a solution of 3.18 g benzaldehyde (30 mmol) and 1.22 g HCN (45 mmol) in 25 ml of MtBE are added 23.6 ml. of 0.01 molar aqueous citrate buffer solution pH 5.0 and 1.4 ml of S-hydroxynitrile lyase solution, containing 20.3 mg of enzyme (E.C. 4.1.2.11). The mixture is stirred for 60 minutes at room temperature. The two phases are separated. The aqueous layer is extracted with 25 ml of MtBE. The organic layers are combined and concentrated by evaporation under reduced pressure, yielding the desired S-mandelonitrile. Yield 84%, enantiomeric excess 98%.

In a corresponding manner is prepared the S-cyanohydrin derivative of 4-hydroxybenzaldehyde (yield 94%, ee 98%) Tb procedure is also applied to 5-methylfurfural, 4-methoxybenzaldehyde and piperonal.

EXAMPLE IV

Recycling of enzyme solution.

To a solution of benzaldehyde (3.18 g; 30 mmol) and hydrogen cyanide (1.22 g; 45 mmol) in 25 ml of MTBE are added 25 ml 0.01 molar citrate buffer solution pH 5.5 and R-hydroxynitrile lyase solution containing 13.3 mg enzyme. The two phases are properly mixed at room temperature for 20 to 25 minutes.

After separation of the layers, the organic phase is worked up in the usual way, whereas the aqueous phase is added to a fresh solution of benzaldehyde and hydrogen cyanide as described above. This procedure is repeated three times. Yields of product and purities are given in Table below.

TABLE B

| Cycle nr | Yield (%) | ee (%) |
|---|---|---|
| 1 | 95 | >99 |
| 2 | 95 | >99 |
| 3 | 95 | >99 |
| 4 | 94 | >99 |

EXAMPLE V

The influence of variations in pH and temperature are investigated in the conversion of 4-methoxybenzaldehyde in a corresponding manner as described in Example I. To be able to observe differences in conversion as a result of said variations, the reactions are stopped before the conversions are complete, viz. after 2 hours. The following results are obtained: Table C.

TABLE C

| reaction conditions | | results | |
|---|---|---|---|
| pH | temp. (°C.) | conversion (%) | ee (%) |
| 5.5 | 10 | 70 | 96 |
| 4.5 | 10 | 61 | 99 |
| 4.5 | 30 | 79 | 98 |

EXAMPLE VI

The conversion of benzaldehyde to R-mandelonitrile is determined in the biphasic solvent system of the invention, using different organic solvents.

Standardized conditions:
25 ml organic solvent
25 ml 50 mM citrate buffer, pH 5.0
3.18 g (30 mmol) benzaldehyde
0.5 ml aqueous solution of R-hydroxynitrile lyase (7.5 rag)
1.22 g HCN (45 mmol)
T = 20° C.

The results are presented in Table below.

TABLE D

| org. solvent | reaction time (min) | conv. (%) | ee (%) | % (50) | through-put (%) |
|---|---|---|---|---|---|
| methyl t.butyl ether | 40 | 98 | >99 | 1.0 | 0.9 |
| methyl i.butyl ketone | 40 | 98 | >99 | 1.1 | 0.9 |
| ethyl acetate | 20 | >99 | >99 | 1.0 | 1.8 |
| diisopropyl ether | 10 | >99 | >99 | 1.3 | 3.6 |
| n-butyl acetate | 5 | >99 | >99 | 1.3 | 7.2 |

EXAMPLE VII

Process for the preparation of R-mandelonitrile, including HCN-extraction procedure. To a solution of 58.8 g NaCN (1.2 mol) in 150 ml water are added 450 ml methyl tert.butyl ether (MTBE). Then 90 g 80% acetic acid are added. The mixture is stirred for 5 min and the layers are separated. To the organic layer are successively added a solution of 172.5 rag oxynitrilase in 500 ml 100 mM citrate buffer (pH 5.5) and 73.7 g benzaldehyde. The reaction mixture is stirred at room temperature for 20 min. The layers are separated and the MTBE layer is dried over $Na_2SO_4$, filtered and evaporated to dryness. The desired R-mandelonitrile is obtained in a yield of 92.0 g (99.5%). The enantiomeric excess (ee) is 96%.

$$\eta_0(50) = 350,000/(2 \times 172.5 \times 1360) = 0.75$$

The throughput is 2.1.

EXAMPLE VIII

4-Hydroxybenzaldehyde is a notoriously difficult substrate for the preparation of the corresponding optically active cyanohydrin. The method of the present invention, however, is also suitable for the conversion of this substrate, as will be clear from the following example.

To a mixture of 25 ml 50 mM citrate buffer (pH 5.0) and 25 ml MTBE are successively added 3.0 ml (45 mg) oxynitrilase solution and 1.22 g (10 mmol) 4-hydroxybenzaldehyde. Then 2.70 g HCN (100 mmol) are added, and the reaction mixture is stirred at 10° C. for 7 hours. After separation of the layers and extraction of the aqueous layer with 20 ml MTBE, the combined organic layers are evaporated to dryness. The desired optically active cyanohydrin is obtained in a yield of 93% (ee=94%).

EXAMPLE A

The following comparative experiments are carried out.

A1: In a reaction vessel are combined 25 ml ethyl acetate, saturated with water, and 3 g of an immobilized enzyme. The enzyme preparation comprises 44 mg hydroxynitrile lyase, immobilized on 1 g Eupergit C®, a functionalized organic polymeric carrier, and 2 g 0.1 molar citrate buffer solution (pH 5.5).

To this mixture are added 0.53 g benzaldehyde (5 mmol) and 0.35 g HCN (13 mmol). Stirring for 20 min. at room temperature, filtration of the carrier (enzyme preparation) and washing of the carrier with ethyl acetate, followed by the usual work-up procedure yields the desired cyanohydrin enantiomer in a yield of 98%; 50% conversion after 4.7 min.

$$\overline{V}(50) = 2500/(4.7 \times 44) = 12.1$$
$$\eta_0(50) = 12.1/1360 = 0.009$$

The throughput, a measure for the production capacity, is 0.60 (in $mol.l^{-1}.h^{-1}$).

A2: In a corresponding manner as described in Example A1 the above conversion is investigated, this time, however, with MTBE instead of ethyl acetate. The desired product is obtained in a yield of 85%.

$\overline{V}(50) = 16$  $\eta_0(50) = 0.012$  *Throughput:* 0.6

A3: In a corresponding manner as described in Example A1 the above conversion is investigated, this time, however, with 600 mg of the enzyme preparation (8.6 mg immobilized enzyme) in a 30% v/v DMF/water mixture. Yield of cyanohydrin enantiomer 80%; 90% ee.

$\overline{V}(50)=60 \; \eta_0(50)=0.044$ Throughput: 0.6

A4: A reaction vessel is charged with 25 ml 30% v/v DMF/water mixture. To this mixture are added 0.53 g benzaldehyde (5 mmol) ad 0.35 g HCN (13 mmol). Then 700/μl of an enzyme solution, containing 7.8 mg hydroxynitrile lyase are added. Stirring for 20 minutes at room temperature and usual work-up procedure yields the desired product a yield of 71%; 99% ee.

$\overline{V}(50)=119 \; \eta_0(50)=0.087$ Throughput: 0.6

A5: The same reaction is carried out as described in Example A4, this time however with a 30% v/v ethanol/water mixture instead of DMF/water.
Yield 82%; >98% ee.

$\overline{V}(50)=84 \; \eta_0(50)=0.063$ Throughput: 0.6

A6: Exactly as described in Example I of the above-mentioned EP-A-276375, an immobilized enzyme preparation is prepared: hydroxynitrile lyase, acetate buffer, AVICEL ® cellulose. The enzyme preparation is suspended into 25 ml ethyl acetate, saturated with 10 mmol aqueous acetate buffer solution (pH 5.4). To this suspension are added 0.53 g benzaldehyde (5 mmol) and 250 l HCN (6.5 mmol). After stirring for 2.5 hours at room temperature the enzyme preparation is filtered off and the filtrate is worked up in a usual manner. Less than 1% conversion to the desired cyanohydrin enantiomer was observed.

A7: The experiment described in Example A6 is repeated, this time, however, by using an enzyme preparation prepared in a different manner as described in EP-A-276375: pressing and drying the final enzyme preparation was omitted. The enzyme preparation comprises 1.8 mg hydroxynitrile lyase. The conversion is followed by UV—spectroscopy during the reaction period. The following conversion is observed: Table E.

TABLE E

| t (min.) | conv. | t (min.) | conv. |
|---|---|---|---|
| 0 | — | 45 | 34 |
| 5 | 0 | 60 | 44 |
| 10 | 13 | 90 | 53 |
| 20 | 22 | 120 | 58 |
| 30 | 29 | 150 | 64 |

From the above results it appears that a 50% conversion is reached after 78 min.

$\overline{V}(50)=2500/(7.8\times1.8)=17.8$
$\eta_0(50)=17.8/1360=0.0013$

The throughput is 0.08.

A8: Exactly as described in example I of the above-mentioned EP-A-446826, the conversion of benzaldehyde to R-mandelonitrile is carried out: 280 μl enzyme solution (conc. 10 mg enzyme/ml) containing 2.8 mg enzyme; 100 mg substrate=940 mol. The reaction is continued for 50 min, yielding the desired isomer in an optical purity (ee) of 99%. During this period the conversion is followed by GC. A conversion of 50% is reached after 1 min, a conversion of 95% after 10 min.

$\overline{V}(50)=470/(1\times2.8)=167.8$
$\eta_0(50)=167.8/1360=0.12$

We claim:
1. A method of preparing an optically active cyanohydrin by addition of hydrogen cyanide to a carbonyl compound, selected from aldehydes and ketones which allow addition of hydrogen cyanide, in a biphasic solvent system, comprising a homogeneous aqueous solution of hydroxynitrile lyase, and a suitable organic solvent which is at least substantially immiscible with water, said method being characterized in that said homogeneous aqueous solution is buffered with a buffer solution having a pH between 3 and 6, said buffer solution being selected from an acetate buffer and a non-acetate buffer, wherein said acetate buffer has a buffer concentration of between 0.005 and 0.1 mole per liter and wherein said non-acetate buffer is selected from citrate, succinate, glutamate and phthalate buffers, that the volume ratio organic phase:aqueous phase is between approx. 5:1 and approx. 1:5, and that a solution of hydrogen cyanide and said carbonyl compound in said organic solvent is properly mixed to ensure sufficient interfacial area between the phases during the reaction period with said homogeneous aqueous solution of hydroxynitrile lyase.

2. A method as claimed in claim 1, characterized in that the volume ratio organic phase:aqueous phase varies between approx 3:1 and approx 1:3.

3. A method as claimed in claim 1 or 2, characterized in that the concentration of the non-acetate buffer is between 0.005 and 0.5 mole per liter and that the pH of the buffer solution is between approx. 4 and approx. 5.5.

4. A method as claimed in claim 3, characterized in that the buffer is selected from the group consisting of citrate, succinate, glutamate and phthalate buffer.

5. A method as claimed in claim 4, characterized in that to a solution of hydrogen cyanide in said organic solvent are successively added said homogeneous buffered solution of hydroxynitrile lyase and said carbonyl compound, after which the biphasic reaction system, thus obtained, is properly mixed during the reaction period.

6. A method as claimed in claim 1 wherein the organic solvent is selected from the group consisting of di($C_1$-$C_6$)alkyl ethers, ($C_1$-$C_5$)carboxylic-($C_1$-$C_5$)alkyl esters, di($C_1$-$C_5$)alkyl ketones, ($C_4$-$C_8$)aliphatic alcohols, and mixtures of these solvents with each other or with apolar diluents.

7. A method as claimed in claim 6, wherein the organic solvent is selected from diethyl ether, di-n-propyl ether, di-isopropyl ether, di-n-butyl ether, di-isobutyl ether, methyl-t-butyl ether, n-propyl acetate, ethyl acetate, isopropyl acetate, isomeric butyl acetates, isomeric amyl acetates, methylethylketone, diethylketone, methylisobutylketone, and a mixture of these solvents with each other or with an apolar diluent selected from aromatic hydrocarbons, aliphatic hydrocarbons and chlorinated aromatic or aliphatic hydrocarbons.

8. A method as claimed in claim 7, wherein the organic solvent is selected from n-propyl acetate, isopropyl acetate, n-butyl acetate, isobutyl acetate, sec.-butyl acetate and amyl acetate.

9. A method as claimed in claim 6, 7 or 8, characterized in that the concentration of said carbonyl compound in said organic solvent is more than 5% wt./vol.

10. A method as claimed in claim 1, characterized in that after the reaction period the aqueous phase is separated from the organic phase and is reused at least once by properly mixing said aqueous phase with a fresh solution of hydrogen cyanide and said carbonyl compound in said organic solvent during another reaction period.

11. A method as claimed in claim 3, wherein the concentration of the non-acetate buffer is between 0.01 and 0.2 mole per liter.

12. A method of preparing an optically active cyanohydrin by addition of hydrogen cyanide to a carbonyl compound, selected from aldehydes and ketones which allow addition of hydrogen cyanide, in a biphasic solvent system, comprising a homogeneous aqueous solution of hydroxynitrile lyase, and a suitable organic solvent which is at least substantially immiscible with water, said method being characterized in that said homogeneous aqueous solution is buffered with a buffer solution having a pH between 3 and 6, said buffer solution being selected from an acetate buffer and non-acetate buffer, wherein said acetate buffer has a buffer concentration of between 0.005 and 0.1 mole per liter and wherein said non-acetate-buffer is selected from citrate, succinate, glutamate and phthalate buffers, that the volume ratio organic phase:aqueous phase is between approx. 3:1 and 1:3, and that a solution of hydrogen cyanide and said carbonyl compound in said organic solvent is properly mixed to ensure sufficient interfacial area between the phase during the reaction period with said homogeneous aqueous solution of hydroxynitrile lyase.

* * * * *